(12) United States Patent
Zeijlstra et al.

(10) Patent No.: US 9,795,755 B2
(45) Date of Patent: Oct. 24, 2017

(54) PATIENT INTERFACE

(71) Applicant: KONINKLIJKE PHILIPS N.V., Eindhoven (NL)

(72) Inventors: Harmina Christina Zeijlstra, Breda (NL); Antonius Adrianes Petrus Schudelaro, Tilburg (NL); Richard Johannus Maria Van De Ven, Noord Brabant (NL); Sander Theodoor Pastoor, Ultrecht (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 346 days.

(21) Appl. No.: 14/413,528

(22) PCT Filed: Jul. 1, 2013

(86) PCT No.: PCT/IB2013/055376
§ 371 (c)(1),
(2) Date: Jan. 8, 2015

(87) PCT Pub. No.: WO2014/009841
PCT Pub. Date: Jan. 16, 2014

(65) Prior Publication Data
US 2015/0174356 A1 Jun. 25, 2015

Related U.S. Application Data

(60) Provisional application No. 61/670,245, filed on Jul. 11, 2012.

(51) Int. Cl.
*A61M 16/06* (2006.01)

(52) U.S. Cl.
CPC ........ *A61M 16/0644* (2014.02); *A61M 16/06* (2013.01); *A61M 16/0622* (2014.02); *A61M 16/0655* (2014.02); *A61M 16/0683* (2013.01)

(58) Field of Classification Search
CPC ................................. A61M 16/0633–16/0655
See application file for complete search history.

(56) References Cited

U.S. PATENT DOCUMENTS

2007/0175480 A1* 8/2007 Gradon ............ A61M 16/0638
128/207.11
2008/0314390 A1* 12/2008 Kwok ............... A61M 16/0683
128/207.11

(Continued)

FOREIGN PATENT DOCUMENTS

DE          10155152 A1    6/2002
EP          1205205 A2     5/2002
(Continued)

*Primary Examiner* — Valerie L Woodward
(74) *Attorney, Agent, or Firm* — Michael W. Haas

(57) ABSTRACT

The invention provides a patient interface (10) comprising a patient interface element (12, 14, 15) for delivering breathing gas to a patient, and a forehead support (30). One of the forehead support and the patient interface element comprises a shaft (50) and the other comprises a hollow tube (51) in which the shaft is received, with the shaft slidable within the tube to permit adjustment of the position of the forehead support relative to the patient interface. The shaft and hollow tube are rotatable between a free and locked configuration. This provides a simple to use adjustment mechanism with few components.

14 Claims, 4 Drawing Sheets

(a)

(b)                (c)

(56) References Cited

U.S. PATENT DOCUMENTS

| | | | | |
|---|---|---|---|---|
| 2010/0000542 A1* | 1/2010 | Chu | .................... | A61M 16/06 128/206.21 |
| 2011/0094516 A1* | 4/2011 | Chang | .................. | A61M 16/06 128/206.28 |
| 2011/0162654 A1 | 7/2011 | Carroll | | |
| 2012/0111333 A1* | 5/2012 | Eifler | ................ | A61M 16/0683 128/205.25 |
| 2012/0266873 A1* | 10/2012 | Lalonde | ............ | A61M 16/0057 128/201.13 |

FOREIGN PATENT DOCUMENTS

| | | |
|---|---|---|
| EP | 1900389 A2 | 3/2008 |
| EP | 2601993 A1 | 6/2013 |
| JP | 5671511 | 6/1981 |
| JP | 2000205220 A | 7/2000 |
| RU | 2388884 C2 | 10/2008 |
| WO | 9407038 A1 | 3/1994 |
| WO | WO2006021085 A2 | 3/2006 |
| WO | WO2010133218 A2 | 11/2010 |
| WO | WO2011060479 A1 | 5/2011 |

* cited by examiner (a)

(b)

(c)

PATIENT INTERFACE

CROSS-REFERENCE TO RELATED APPLICATIONS

This patent application claims the priority benefit under 35 U.S.C. §371 of international patent application no. PCT/IB2013/055376, filed Jul. 1, 2013, which claims the priority benefit under 35 U.S.C. §119(e) of U.S. Provisional Application No. 61/670,245 filed on Jul. 11, 2012, the contents of which are herein incorporated by reference.

FIELD OF THE INVENTION

The present invention relates to patient interfaces for transporting a gas to and/or from an airway of a user.

BACKGROUND OF THE INVENTION

There are numerous situations where it is necessary or desirable to deliver a flow of breathing gas non-invasively to the airway of a patient, i.e. without inserting a tube into the airway of the patient or surgically inserting a tracheal tube in their oesophagus. For example, it is known to ventilate a patient using a technique known as non-invasive ventilation. It is also known to deliver continuous positive airway pressure (CPAP) or variable airway pressure, which varies with the patient's respiratory cycle, to treat a medical disorder, such as sleep apnoea syndrome, in particular, obstructive sleep apnoea (OSA).

Non-invasive ventilation and pressure support therapies involve the placement of a patient interface comprising a mask component on the face of a patient. The mask component may be, without limitation, a nasal mask that covers the patient's nose, a nasal pillow/cushion having nasal prongs that are received within the patient's nostrils, a nasal/oral mask that covers the nose and mouth, or a full face mask that covers the patient's face. The patient interface interfaces between the ventilator or pressure support device and the airway of the patient, so that a flow of breathing gas can be delivered from the pressure/flow generating device to the airway of the patient.

Such assemblies are typically maintained on the face of a patient by headgear having one or more straps adapted to fit over/around the patient's head.

FIG. 1 shows a typical system to provide respiratory therapy to a patient. This system will be referred to in the description and claims as a "patient interface assembly".

The assembly 2 includes a pressure generating device 4, a delivery conduit 16 coupled to an elbow connector 18, and the patient interface 10. The pressure generating device 4 is structured to generate a flow of breathing gas and may include, without limitation, ventilators, constant pressure support devices (such as a continuous positive airway pressure device, or CPAP device), variable pressure devices, and auto-titration pressure support devices.

Delivery conduit 16 communicates the flow of breathing gas from pressure generating device 4 to patient interface 10 through the elbow connector 18. The delivery conduit 16, elbow connector 18 and patient interface 10 are often collectively referred to as a patient circuit.

The patient interface includes a patient interface element which is a mask 12 in the form of a shell 15 and cushion 14, which in the exemplary embodiment is a nasal and oral mask. However, any type of mask, such as a nasal-only mask, a nasal pillow/cushion or a full face mask, which facilitates the delivery of the flow of breathing gas to the airway of a patient, may be used as mask. The cushion 14 is made of a soft, flexible material, such as, without limitation, silicone, an appropriately soft thermoplastic elastomer, a closed cell foam, or any combination of such materials.

An opening in the shell 15, to which elbow connector 18 is coupled, allows the flow of breathing gas from pressure generating device 4 to be communicated to an interior space defined by the shell 15 and cushion 14, and then to the airway of a patient.

The patient interface assembly 10 also includes a headgear component 19, which in the illustrated embodiment is a two-point headgear. Headgear component 19 includes a first and a second strap 20, each of which is structured to be positioned on the side of the face of the patient above the patient's ear.

Headgear component 19 further includes a first and a second mask attachment element 22 to couple the end of one of the straps 20 to the respective side of mask 12.

A problem with this type of assembly is that the headgear force vectors necessary to achieve a robust and stable seal against the face of the patient can cut a straight line near the corners of a patient's eyes, which can be uncomfortable and distracting.

In order to avoid this, it is well known to include as part of the patient interface a forehead support to spread the required forces over a larger area. In this way, an additional cushion support on the forehead balances the forces put by the mask around the nose or nose and mouth.

All faces are different to each other. When using a patient interface assembly which has a forehead support, this forehead support should be adjustable for personal fit. The offset between facial plane and the forehead support can differ in the range of 30 mm. An example of known adjustment arrangement uses a rotating mechanism, controlled by a rotary knob. This mechanism results in an increase or decrease of the offset between the facial plane and the forehead support. The user has to rotate the knob to get the right offset and the right fit.

From an ergonomics perspective, rotating a knob is not the most convenient way to implement adjustment. The number of elements and required accuracy is costly and the assembly can be noise due to play between components.

SUMMARY OF THE INVENTION

According to the invention, there is provided an assembly as claimed in claim 1.

In one aspect, the invention provides a patient interface comprising:

a patient interface element for delivering a breathing gas to a user; and a forehead support coupled to the patient interface element, wherein one of the forehead support and the patient interface element comprises a shaft and the other of the forehead support and the patient interface element comprises a hollow tube in which the shaft is received, with the shaft slidable within the tube to permit adjustment of the position of the forehead support relative to the patient interface element, wherein the shaft and hollow tube are rotatable relative to each other between a free configuration in which the shaft can be slid within the tube and a locked configuration in which the sliding of the shaft within the tube is blocked.

This arrangement provides sliding adjustment of the position of the forehead support. This enables the desired position to be reached quickly and easily. For example, the forehead support can simply be pushed from a refracted position to a position in which it contacts the forehead, and then be locked in place. The locking is achieved by relative rotation, and can thus be a simply rotation of a knob or lever through a small angle, for example less than 90 degrees. By avoiding full rotation of a control knob or lever, the task is more comfortable for the patient.

The shaft can have a cross sectional shape which fits within the tube with clearance around it in the rotational position corresponding to the free configuration, but has vertices which engage with the inner surface of the tube in the rotational position corresponding to the locked configuration. Thus, the locking is a wedging of one shape within another.

The shaft and the inner surface of the tube can each have the same polygonal shape, with the size of the inner surface of the tube greater than the size of the shaft. In the wedged configuration, the vertices of the smaller polygon mate with the sides of the larger polygon.

The polygonal shape can be a triangle. This means the rotation between configurations can be only 60 degrees—the angle between one vertex and the middle of one side face.

The forehead support can be mounted such that relative rotation between the forehead support and the patient interface element is inhibited. Thus, only sliding adjustment is made and the relative rotation is only for the locking function.

The shaft can be attached to the forehead support and the tube is then rotationally mounted to the patient interface, and the tube has a control lever to enable the user to control rotation of the tube between the free and locked configurations. The control lever can extend outwardly from the tube in a radial direction. This gives leverage to make the rotation function easy for the patient.

Alternatively, again with the shaft attached to the forehead support and the tube rotationally mounted to the patient interface, the tube can have a control knob to enable the user to control rotation of the tube between the free and locked configurations.

BRIEF DESCRIPTION OF THE DRAWINGS

Examples of the invention will now be described in detail with reference to the accompanying drawings, in which.

DETAILED DESCRIPTION OF THE EMBODIMENTS

The invention provides a patient interface comprising a patient interface element for delivering breathing gas to a user (i.e. a mask) and a forehead support. One of the forehead support and the patient interface element comprises a shaft and the other of the forehead support and the patient interface comprises a hollow tube in which the shaft is received, with the shaft slidable within the tube to permit adjustment of the position of the forehead support relative to the patient interface. The shaft and hollow tube are rotatable between a free and locked configuration. This provides a simple to use adjustment mechanism with few components.

Figure 1:
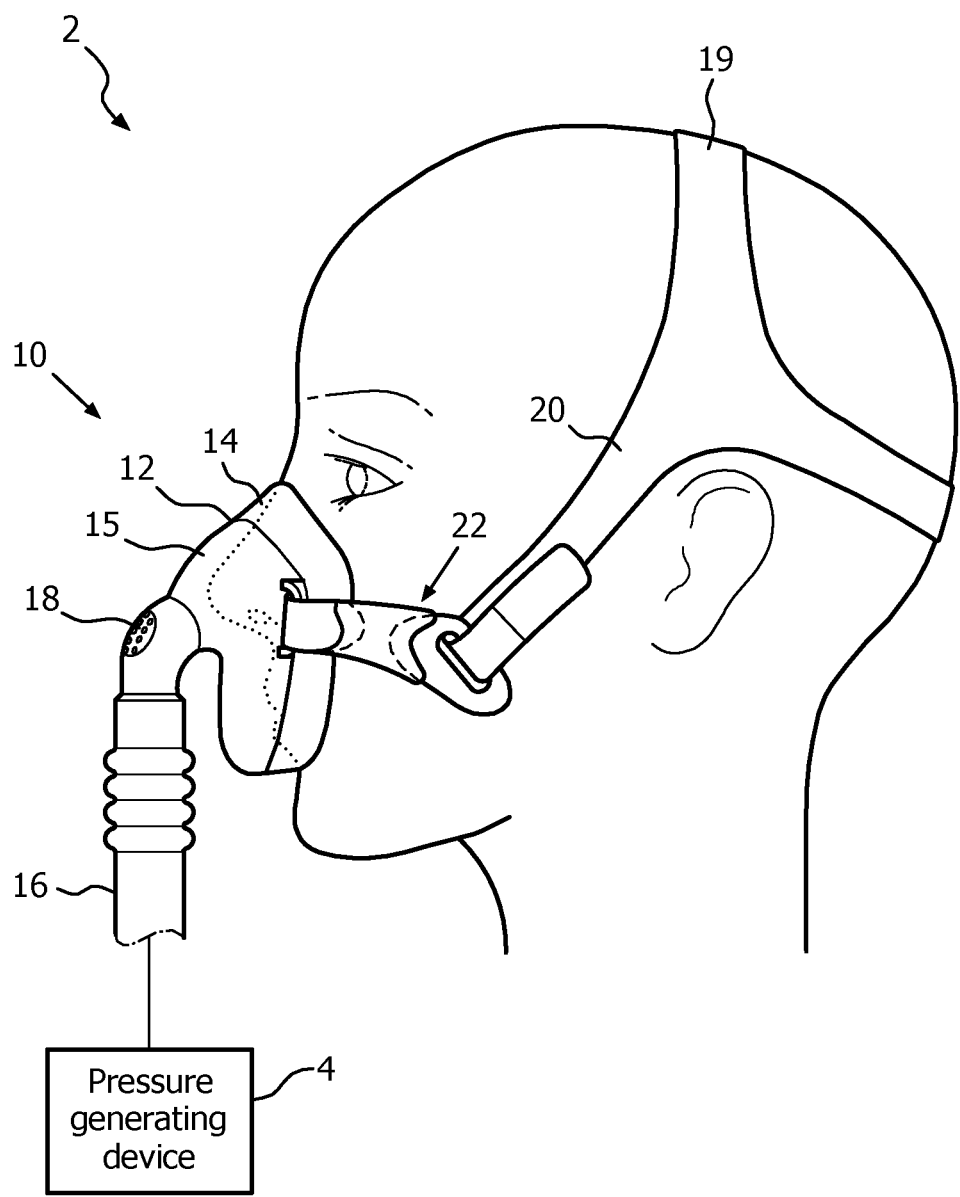
FIG. 1 shows a known patient interface.
Figure 2:
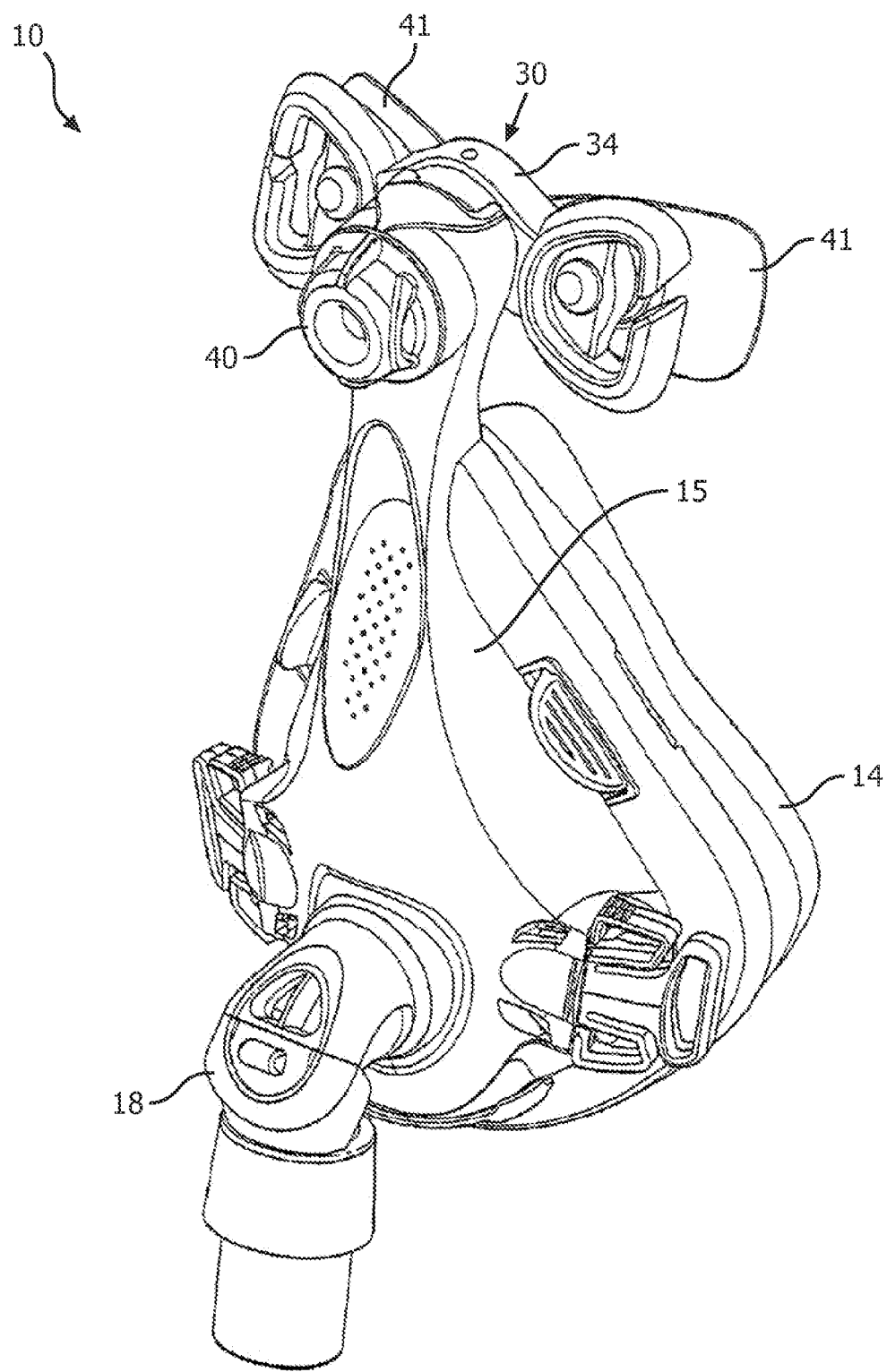
FIG. 2 shows a known patient interface as disclosed in US2010/0000542.

FIG. 2 is taken from US2010/0000542 and shows a patient interface assembly in the form of a full facial mask assembly 10 including a forehead support 30. The patient interface element (the mask part) is for delivering gas to the user and includes a frame 16, a cushion 14 adapted to form a seal with the patient's face, an elbow assembly 18 for connection to an air delivery tube (components 10,14,16,18 corresponding to those of the same number in FIG. 1).

FIG. 2 shows a forehead support 30 for reducing the forces on the patient's face, and including a frame 34 which carries forehead support cushions 41. In this example, the position of the forehead support is adjustable by a rotary knob 40.

The rotary knob comprises a screw-type actuator which moves the forehead support 30 along a generally linear path. The rotary adjustment knob 40 includes a threaded shaft, and the forehead support frame 34 includes an internally threaded tube.

When the adjustment knob 40 is rotated, the internally threaded tube of the forehead support 34 extends or retracts from the threaded shaft of the adjustment knob 40, which causes adjustable movement of the forehead cushions 41.

Figure 3:
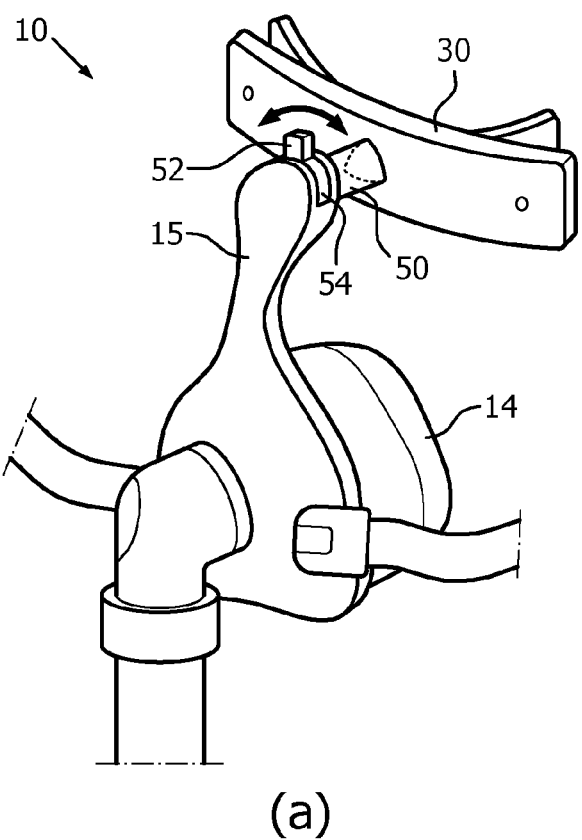
FIG. 3 shows a first example of interface of the invention.
Figure 3:
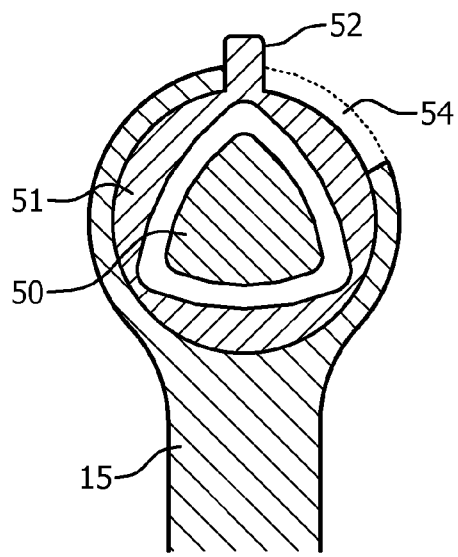
Figure 3:
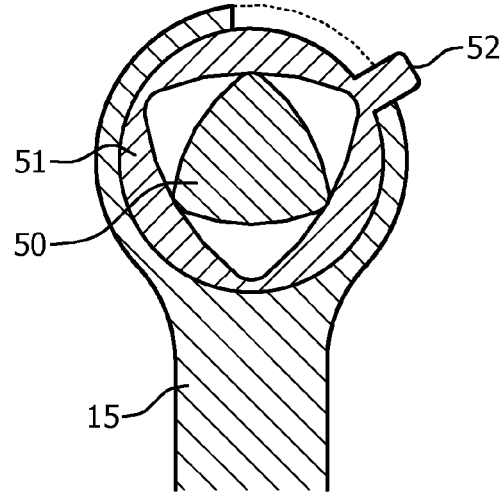

FIG. 3 shows a first example of patient interface of the invention, similar in structure to the design of FIG. 2, with a cushion 14 and shell 15 and a forehead support 30.

FIG. 3a shows the patient interface in perspective view. FIG. 3b shows a cross section of the locking arrangement in a free configuration and FIG. 3c shows a cross section of the locking arrangement in a locked configuration.

The forehead support 30 is connected to a shaft 50 which is received within a tube 51 formed as part of the shell 15 (which in this example is a rigid frame part of the mask).

The tube 51 has a central opening in which the shaft 50 is received. The tube 51 only requires a length sufficient to hold the forehead support in a lock configuration as explained below. A rotary switch 52 controls locking of the system, and the locking switch is in the form of a lever which is guided within a slot 54 of the shell 15. This lever 52 controls rotation of the tube 51. However, the shaft 50 is unable to rotate. For example, an additional coupling (not shown) is provided between the forehead support 30 and the mask shell 15 which only allows sliding movement. This can be a guide within a guide channel running along the axial direction of the shaft 50, or a pin received within a slot. Any suitable coupling between the forehead support and the mask shell can be used which allows the linear adjustment but prevents relative angular movement.

Thus, rotation of the lever 52 causes relative rotation between the shaft and tube. When unlocked, the user can adjust the distance to the forehead support by simply controlling linear sliding between the forehead support 30 and the mask shell.

The locking function is based on a wedging interaction, i.e. locking by form.

In this example, the shaft 50 has a triangular cross section (e.g. an equilateral triangle) and the internal opening of the tube has the same shape but slightly larger. This means that when the two triangles have the same angular position, there is clearance between them as shown in FIG. 3b.

The centre to vertex distance of the smaller triangle is equal or slightly larger than the centre to side distance of the larger triangle (i.e. the straight distance from the centre to the middle of one side), so that when the triangular shaft is rotated by 60 degrees, it is wedged with the tube as shown in FIG. 3c.

The shaft 50 maintains its angular orientation by the coupling between the forehead support and the mask frame 15.

This embodiment uses a triangular shape but the shape can be any polygon, for example a pentagon. For a regular polygon, the centre to vertex distance of the smaller shaft is the same or slightly larger than the centre to side distance of the larger opening, for wedging to be effective.

Figure 4:
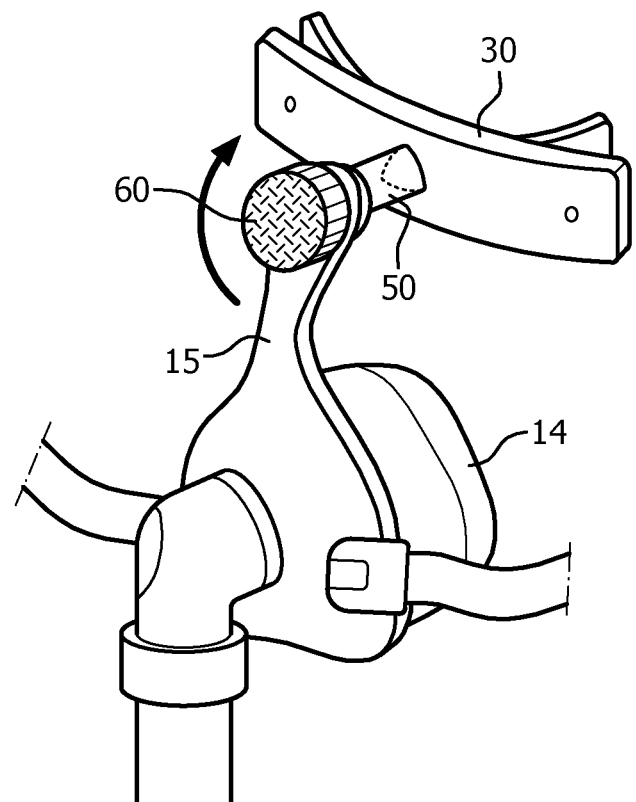
FIG. 4 shows a second example of interface of the invention.
Figure 4:
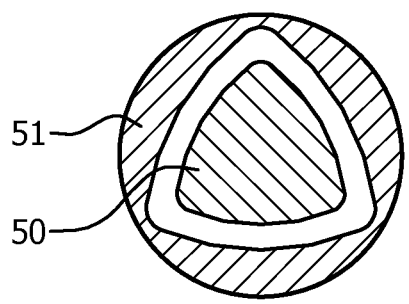
Figure 4:
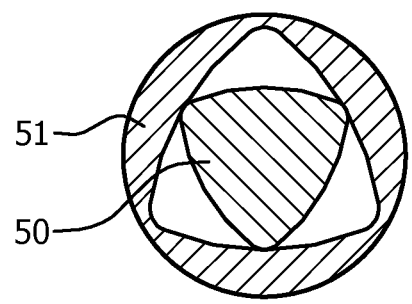

FIG. 4 shows a second example of patient interface assembly of the invention, similar in structure to the design of FIG. 2, with a cushion 14 and shell 15 and a forehead support 30.

FIG. 4a shows the assembly in perspective view. FIG. 4b shows a cross section of the locking arrangement in a free configuration and FIG. 4c shows a cross section of the locking arrangement in a locked configuration.

The same reference numerals are used as in FIG. 3. Instead of a rotary switch, a rotary knob is used.

The shaft 50 is coupled to a locking knob 60, and the triangular (or other shape) shaft 50 is connected to the forehead support 30. In this example, the shaft is rotated to effect the locking. This means the shaft needs to be able to rotate relative to the forehead support, since the shaft rotation should not cause rotation of the forehead support. The forehead support 30 is again coupled to the mask frame to prevent relative rotation but allow linear adjustment in the same way as explained above, but the shaft is further rotatable relative to the forehead support to which it is connected. Thus, the locking function locks and releases the linear adjustment. The angular position of the forehead support remains constant during the locking and unlocking functions as well as during the linear adjustment. In the two examples above, the forehead support has the shaft and the mask frame has the tube. However, these roles may be reversed.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. Any reference signs in the claims should not be construed as limiting the scope.

The invention claimed is:

1. A patient interface comprising:
a patient interface element for delivering a breathing gas to a user; and
a forehead support coupled to the patient interface element;
wherein one of the forehead support and the patient interface element comprises a shaft and the other of the forehead support and the patient interface element comprises a hollow tube in which the shaft is received, with the shaft slidable within the tube to permit adjustment of the position of the forehead support relative to the patient interface element,
wherein the shaft and hollow tube are rotatable relative to each other about an axis between a free configuration in which the shaft is capable of sliding along the axis within the tube and a locked configuration in which the sliding of the shaft along the axis within the tube is blocked,
wherein the shaft is positionable in the locked configuration in a first position along the axis within the tube,
wherein the shaft is positionable in the locked configuration in a second position, different than the first position, along the axis within the tube, and
wherein, when in the free configuration, the shaft is moveable between the first position and the second position by sliding of the shaft along the axis.

2. A patient interface as claimed in claim 1, wherein the rotation angle between the free and locked configurations is less than 90 degrees.

3. A patient interface as claimed in claim 1, wherein the shaft has a cross sectional shape which fits within the tube with clearance around it in the rotational position corresponding to the free configuration, but has vertices which engage with the inner surface of the tube in the rotational position corresponding to the locked configuration.

4. A patient interface as claimed in claim 3, wherein the shaft and the inner surface of the tube each have the same polygonal shape, with the size of the inner surface of the tube greater than the size of the shaft.

5. A patient interface as claimed in claim 4, wherein the polygonal shape is a triangle.

6. A patient interface as claimed in claim 1, wherein the forehead support is mounted such that relative rotation between the forehead support and the patient interface element is inhibited.

7. A patient interface as claimed in claim 6, wherein the shaft is attached to the forehead support and the tube is rotationally mounted to the patient interface, and the tube has a control lever to enable the user to control rotation of the tube between the free and locked configurations.

8. A patient interface as claimed in claim 7, wherein the control lever extends outwardly from the tube in a radial direction.

9. A patient interface as claimed in claim 6, wherein the shaft is attached to the forehead support and the tube is rotationally mounted to the patient interface, and the tube has a control knob to enable the user to control rotation of the tube between the free and locked configurations.

10. A patient interface assembly comprising a patient interface as claimed in claim 1, and headgear for holding the patient interface element and forehead support against the head of the patient.

11. A patient interface comprising:
a patient interface element for delivering a breathing gas to a user; and
a forehead support coupled to the patient interface element;
wherein one of the forehead support and the patient interface element comprises a shaft and the other of the forehead support and the patient interface element comprises a hollow tube in which the shaft is received, with the shaft slidable within the tube to permit adjustment of the position of the forehead support relative to the patient interface element,
characterized in that
the shaft and hollow tube are rotatable relative to each other between a free configuration in which the shaft is capable of sliding within the tube and a locked configuration in which the sliding of the shaft within the tube is blocked, and
the shaft has a cross sectional shape which fits within the tube with clearance around it in the rotational position corresponding to the free configuration, but has vertices which engage with the inner surface of the tube in the rotational position corresponding to the locked configuration.

12. A patient interface as claimed in claim 11, wherein the shaft and the inner surface of the tube each have the same polygonal shape, with the size of the inner surface of the tube greater than the size of the shaft.

13. A patient interface as claimed in claim 12, wherein the polygonal shape is a triangle.

14. A patient interface comprising:
   a patient interface element for delivering a breathing gas to a user; and
   a forehead support coupled to the patient interface element;
   wherein one of the forehead support and the patient interface element comprises a shaft and the other of the forehead support and the patient interface element comprises a hollow tube in which the shaft is received, with the shaft slidable within the tube to permit adjustment of the position of the forehead support relative to the patient interface element,
   wherein the shaft and hollow tube are rotatable relative to each other between a free configuration in which the shaft is capable of sliding within the tube and a locked configuration in which the sliding of the shaft within the tube is blocked,
   wherein the forehead support is mounted such that relative rotation between the forehead support and the patient interface element is inhibited,
   wherein the shaft is attached to the forehead support and the tube is rotationally mounted to the patient interface, and the tube has a control lever to enable the user to control rotation of the tube between the free and locked configurations, and
   wherein the control lever extends outwardly from the tube in a radial direction.

* * * * *